(12) United States Patent
Pujol Ramo et al.

(10) Patent No.: US 8,366,270 B2
(45) Date of Patent: Feb. 5, 2013

(54) METHOD AND SYSTEM FOR THE OBJECTIVE MEASUREMENT OF OCULAR ACCOMMODATION

(75) Inventors: Jaume Pujol Ramo, Barcelona (ES); Sergio Oscar Luque, Barcelona (ES); Mikel Aldaba Arévalo, Barcelona (ES)

(73) Assignee: Universitat Politecnica de Catalunya, Barcelona (ES)

( * ) Notice: Subject to any disclaimer, the term of this patent is extended or adjusted under 35 U.S.C. 154(b) by 98 days.

(21) Appl. No.: 12/990,311

(22) PCT Filed: Apr. 30, 2009

(86) PCT No.: PCT/ES2009/000233
§ 371 (c)(1),
(2), (4) Date: Jan. 14, 2011

(87) PCT Pub. No.: WO2009/133224
PCT Pub. Date: Nov. 5, 2009

(65) Prior Publication Data
US 2011/0109877 A1   May 12, 2011

(30) Foreign Application Priority Data

Apr. 30, 2008 (ES) .................................. 200801315

(51) Int. Cl.
 A61B 3/14    (2006.01)
 A61B 3/10    (2006.01)
 A61B 3/00    (2006.01)
(52) U.S. Cl. ......... 351/206; 351/216; 351/221; 351/246
(58) Field of Classification Search .................. 351/206, 351/216, 221, 246
See application file for complete search history.

(56) References Cited

FOREIGN PATENT DOCUMENTS

| RU | 2 336 802 C2 | 10/2008 |
| WO | WO 03/032824 A1 | 4/2003 |
| WO | WO 03/090612 A1 | 11/2003 |

OTHER PUBLICATIONS

Atchison, David A. et al., "Critical Subjective Measurement of Amplitude of Accommodation," Optometry and Vision Science, vol. 71, No. 11, 1994, pp. 699-706.
Rosenfield, Mark et al., "Clinical Research Note, Repeatability of clinical measurements of the amplitude of accommodation," Ophthal. Physiol. Opt., vol. 16, No. 3, 1996, pp. 247-249.
Thornton, MD, Spencer T., "Letters, Restoring accommodation: What is real and what is pseudo?," J. Cataract Refract Surg, vol. 31, Oct. 2005, pp. 1851-1852.

(Continued)

*Primary Examiner* — Jack Dinh
(74) *Attorney, Agent, or Firm* — RatnerPrestia

(57) ABSTRACT

The invention relates to a method and system for the objective measurement of ocular accommodation. A double-pass ophthalmoscopic system is used which incorporates a periscope allowing the patient to binocularly see real objects in an open field and images of the retinal plane to be recorded on a CCD camera. The method includes obtaining, for different values of accommodation stimulation, a set of retinal images corresponding to different focal values in the retina, obtaining the different focal positions in the retina by moving the two lenses incorporated in the ophthalmoscopic system. The image with the best optical quality is obtained for each set of images and by associating the selected image with the known value of the accommodation stimulation it is possible to objectively measure the accommodation.

11 Claims, 3 Drawing Sheets

OTHER PUBLICATIONS

Product Sheet_irx3TM. Wavefront Aberrometer, http://imagine-eyes.com/downloads/ies_irx3.pdf, 2005.

Wold, Jon E. et al., "Subjective and objective measurement of human accommodative amplitude," J. Cataract Refract Surg., vol. 29, Oct. 2003, pp. 1878-1888.

Santamaria, J. et al., "Determination of the point-spread function of human eyes using a hybrid optical-digital method," J. Optical Society of America, vol. 4, No. 6, Jun. 1987, pp. 1109-1114.

Guirao, Antonio et al., "Average Optical Performance of the Human Eye as a Function of Age in a Normal Population," Investigative Ophthalmology & Visual Science, vol. 40, No. 1, Jan. 1999, pp. 203-213.

Pujol, Jaume et al., "Influence of amount and changes in axis of astigmatism on retinal image quality," J. Opt. Soc. Am., vol. 15, No. 9, Sep. 1998, pp. 2514-2521.

Torrents, A. et al., "Research Note: Double-pass measurements of retinal image quality in monofocal contact lens wearers," Ophthal. Physiol. Opt., vol. 17, No. 4, 1997, pp. 357-366.

Lopez-Gil, Norberto et al., "Retinal image quality in the human eye as a function of the accommodation," Vision Research 38 (1998), pp. 2897-2907.

Takeda, Tsunehiro et al., "Accommodation on Downward Gaze," Optometry and Vision Science, vol. 69, No. 7, 1992, pp. 556-561.

Win-Hall, Dorothy M. et al., "Objective accommodation measurements in prepresbyopic eyes using an autorefractor and an aberrometer," J. Cataract Refract. Surg., May 2008; 34(5): pp. 774-784.

Guell, J.L. et al., "Accommodative IOL's Objective Evaluation Using a Novel Double-Pass Based Instrument," Assoc. for Research in Vision and Ophthalmology, Inc., Apr. 26, 2004.

International Search Report for PCT International Application No. PCT/ES2009/000233 mailed Sep. 24, 2009.

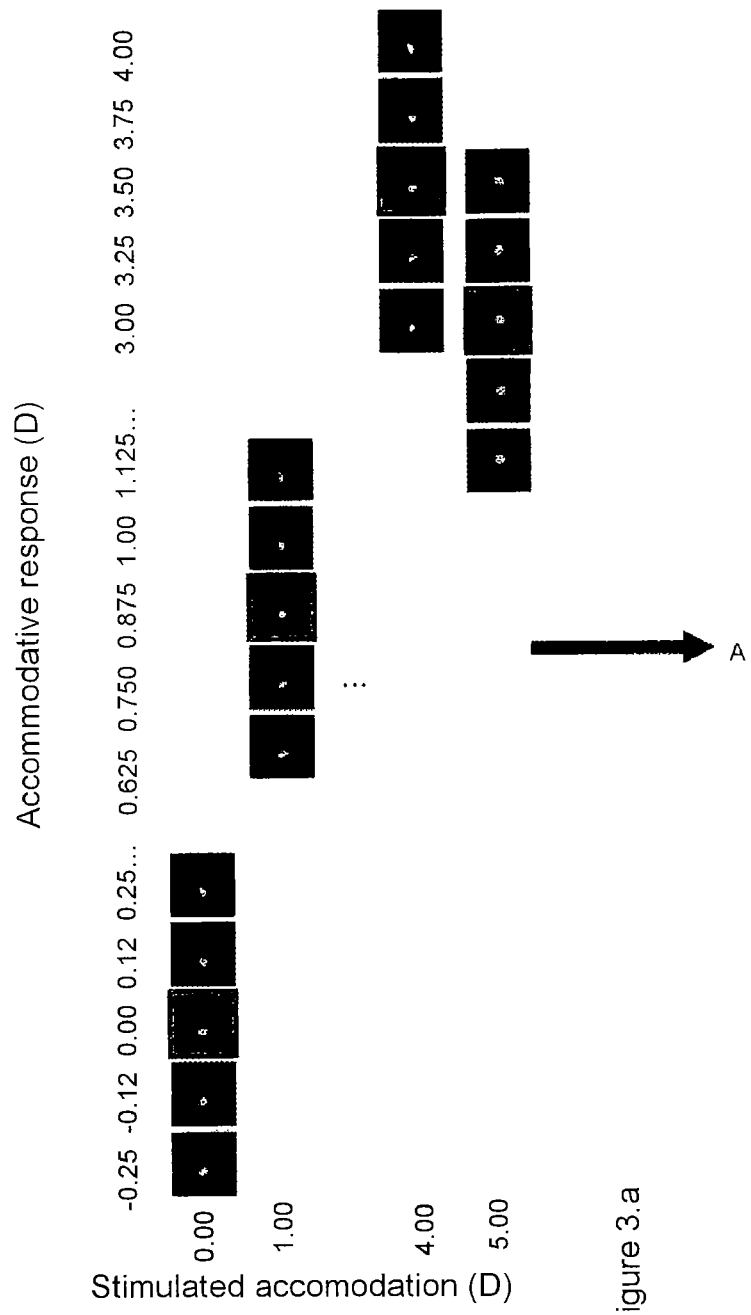
Figure 3.a

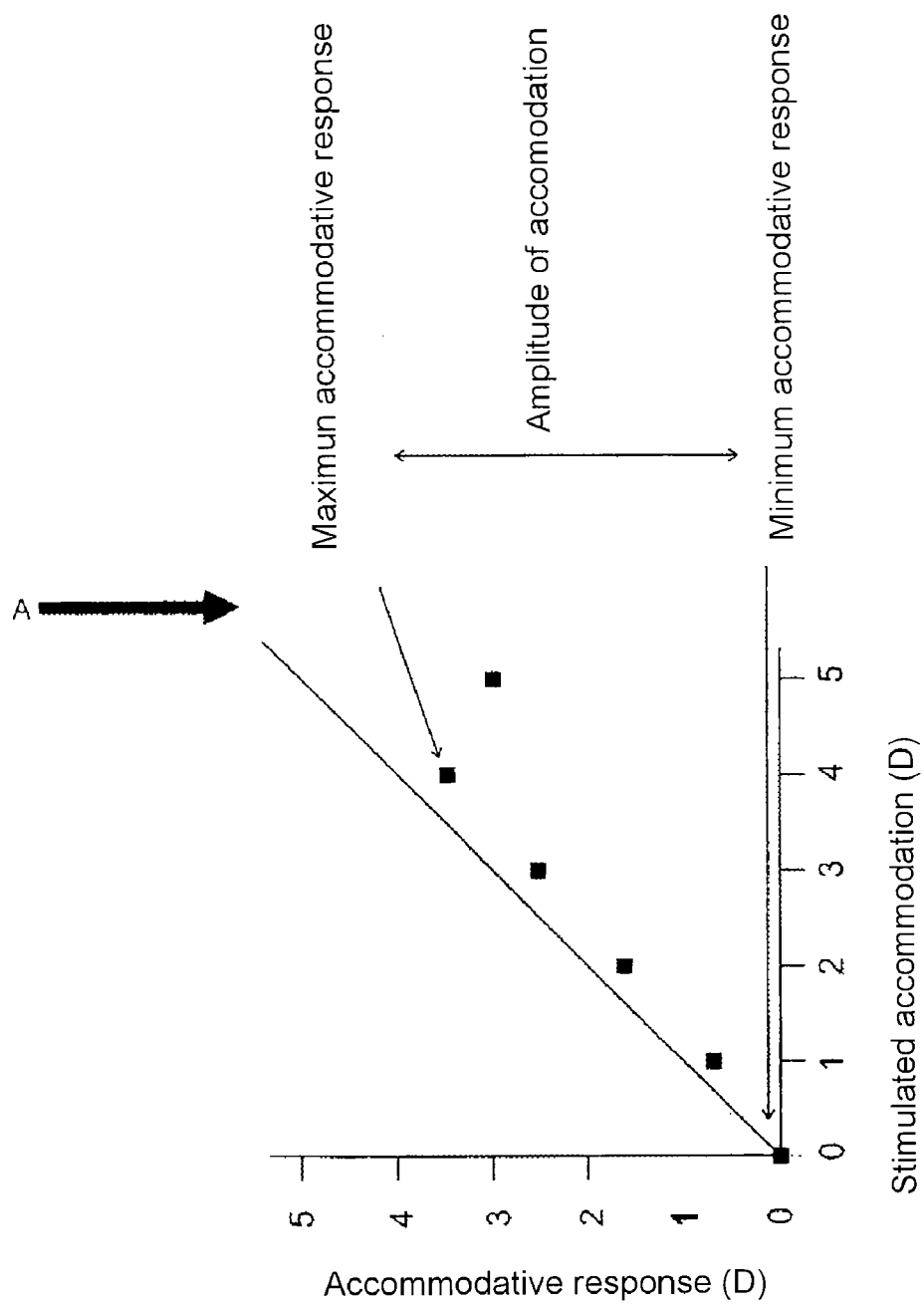
Figure 3.b

METHOD AND SYSTEM FOR THE OBJECTIVE MEASUREMENT OF OCULAR ACCOMMODATION

This application is a U.S. National Phase Application of PCT International Application No. PCT/ES2009/000233, filed Apr. 30, 2009.

FIELD OF THE ART

The present invention relates to a method for the objective measurement of the amplitude of ocular accommodation, which uses a double-pass ophthalmoscopic device and comprises providing an accommodation stimulation and analyzing the response from the images reflected in the retina.

Said stimulation is advantageously provided using negative lenses under far vision conditions or without lenses, modifying the position of the object in a controlled manner.

The proposed method has shown that it can provide a robust technique allowing measurements of accommodation under difficult conditions such as in eyes with cataracts.

The invention also relates to a system integrating the mentioned ophthalmoscopic device to implement the method of the invention.

PRIOR STATE OF THE ART

Accommodation is defined as the dioptric change in the power of the crystalline lens which allows clear vision at different distances. The amplitude of accommodation is the total amount of accommodation that the visual system is capable of putting into effect, and its measurement has a great clinical importance in accommodative problems, binocular vision problems and especially in cases of presbyopia.

The most usual techniques in clinical practice for measuring the amplitude of accommodation have been and are subjective techniques, based on the measurement of visual acuity at different accommodative vergences.

In the push-up method, the starting point is the subjective refraction for far vision of the patient, and an optotype test is placed at a medium distance. The patient is asked to look at the optotype test and the test is slowly moved closer until he or she reports seeing it blurry. The distance from the eye of the patient to the optotype test is measured and the amplitude of accommodation is calculated as the inverse of this distance in meters.

In the negative lens method, the starting point is the subjective refraction for far vision of the patient, and an optotype test is placed at a close distance. The patient is asked to look at the optotype test and negative power lenses are added until the patient reports seeing it blurry. The amplitude of accommodation is the sum of the power in absolute value of the negative lenses plus the inverse of the distance of the optotype test in meters.

These subjective techniques have a series of drawbacks such as the fact of being based on the subjectivity of the response of the patient (D. A. Atchison, E. J. Campbell, K. L. McCabe, "Critical subjective measurement of amplitude of accommodation", Optom. Vis. Sci, 71, 699-706 (1994)), the magnification of the test due to the push-up or to the effect of the negative lenses (M. Rosenfield, A. S. Cohen "Repeatability of clinical measurements of the amplitude of accommodation", Ophthal. Physiol. Opt., 16, 247-249 (1996)) or the effect of pseudoaccommodation (S. P. Thornton, "Restoring accommodation: What is real and what is pseudo?" J. Cataract. Refract. Surg, 31, 1852-1852 (2005)).

Objective methods have been developed in order to solve the problems of the subjective techniques.

Dynamic retinoscopy is based on the measurement of amplitude of accommodation by means of using a retinoscope. The examiner observes the retinoscopic reflex while the accommodation of the patient is stimulated by means of moving an optotype test attached to the retinoscope closer, until finding a significant change in the width of the reflex. The amplitude of accommodation is calculated as the inverse of the distance in meters from the patient to the test at the time at which the change in the retinoscopic reflex takes place.

In the measurements of amplitude of accommodation using aberrometers, measurements of the wavefront are taken at different accommodative vergences. The defocus, which corresponds to $Z_4 = \sqrt{3}(\rho^2 - 1)$ of the Zernike polynomials is calculated from each reading. The measured defocus corresponds to the accommodative error, from which the amplitude of accommodation is calculated by means of an accommodative response curve. Although there are commercial wave sensors offering the possibility of measuring the amplitude of accommodation ("Product sheet_irx3TM. Wavefront Aberrometer" (Available as of Dec. 28, 2007 at http://imagine-eyes.com/downloads/ies_irx3.pdf)), their use has not been extended to clinical practice, which may be due to the existence of various limitations such as the reduction of the pupil diameter with accommodation, for example, a fact which hinders the measurements.

Autorefractometers, automatic instruments for the direct measurement of the ocular refractive state, have also been used to measure the amplitude of accommodation. Measurements of the refraction, which corresponds to the defocus, are taken at several vergences, and the amplitude of accommodation is calculated from the accommodative response curve (J. E. Wold, A. Hu, S. Chen, A. Glasser, "Subjective and objective measurement of human accommodative amplitude", J. Cataract Refract. Surg, 29, 1878-1888 (2003)).

The double-pass technique consists of forming the image of a point source in the retina of the subject and capturing the image of the light reflected in the latter after its double pass through the ocular media. (J. Santamaría, P. Artal, J. Bescos, "Determination of the point-spread function of human eyes using a hybrid optical-digital method", J. Opt. Soc. Am. A, 4, 1109-1114 (1987)). It has been widely used in the study of the optical quality of the human eye (A. Guirao, C. González, M. Redondo, E. Geraghty, S. Norrby, P. Artal, "Average optical performance of the human eye as a function of age in a normal population", Inv. Oph. Vis. Sci., 40, 203-213 (1999), J. Pujol, M. Arjona, J. Arasa, V. Badia, "Influence of amount and changes in axis of astigmatism on retinal-image quality". J. Opt. Soc. Am. A 15, 2514-2521 (1998), A. Torrents, J. Gispets, J. Pujol., "Double-pass measurements of retinal image quality in monofocal contact lens wearers" Ophthal. Physiol. Opt, 17, 357-366 (1997)), and has also been applied in the field of accommodation, concluding that the retinal image quality does not vary significantly during the accommodative process (Norberto López Gil, et al., Vision Research, Volume 38, Edition 19, Jul. 3, 1998 "Retinal image quality in the human eye as a function of the Accommodation").

The document (Norberto López Gil, et al., Vision Research, Volume 38, Edition 19, Jul. 3, 1998 "Retinal image quality in the human eye as a function of the Accommodation"), which contains a number of references to technical literature on accommodation, describes a methodology intended for the same purpose as the present invention and particularly the use of a double-pass apparatus operating with near-infrared light, consisting of a comparison of the images of an unaccommodated eye and those of an accommodated eye.

However, this document neither considers nor suggests the intervention of a controllable external stimulus or the use of specific means for providing it in combination with the mentioned double-pass ophthalmoscopic device, which causes said accommodation to subsequently take a measurement, according to the principles of this invention.

DESCRIPTION OF THE INVENTION

The invention proposes a method for the objective measurement of ocular accommodation, which essentially comprises the following steps:
  a. projecting a spot-light beam on the retina of an eye of a patient;
  b. providing a controlled ocular accommodation stimulation, such that the ciliary muscle of at least said eye is stimulated to generate an accommodative response;
  c. capturing and recording a series of images resulting from the light reflected in the retina of said spot-light beam in correspondence with the response to said stimulus, with a different focus position of the retina; and
  d. selecting, by processing, the image with the best optical quality from among said series of images, the focus value corresponding to the selected image providing the measurement of ocular accommodation.

The invention is based on using an instrument having as a core a double-pass ophthalmoscopic system incorporating a periscope allowing the patient to binocularly see real objects in an open field. The device allows recording images of the retinal plane on a CCD camera. The method consists of obtaining, for different values of accommodation stimulation (provided through the mentioned periscope), a set of retinal images corresponding to different focal values in the retina. The different focal positions in the retina are obtained by means of a system for moving two lenses (Badal system) incorporated in the apparatus. The image with the best optical quality (quality from an optical point of view), i.e., the one having a better MTF (modulation transfer function), is obtained for each set of images and by associating said selected image with the known value of the accommodation stimulation it is possible to objectively measure the accommodation.

The periscopic system incorporated into the double-pass ophthalmoscopic system includes a beam splitter aligned with respect to the point light beam and a mirror associated with an object in an open field The processing of the series of obtained images is carried out by means of an electronic processing system associated with an image capturing system.

According to the proposed method, the mentioned stimulation is carried out on the ciliary muscles of both eyes of said patient, i.e., in a binocular manner, while the mentioned capture and recording are performed on a single eye of the patient.

The stimulation can be performed by means of using negative lenses (Shear Method) or moving the fixation test closer, using the mentioned periscopic system, no substantial differences between the two having been observed in the tests performed.

It has been verified that the use of a commercial double-pass ophthalmoscopic device, modified as has been set forth above (inclusion of a periscopic system and of means for controlled accommodation stimulation therethrough) allows an efficient measurement of the amplitude of accommodation. The method has the advantage of preventing pupil effects present in techniques using other instruments. Furthermore, in comparison with other instruments, the pupil size is not critical and pseudoaccommodation can also be measured and included to count the range when a subject sees objects clearly.

The system proposed by the invention for the objective measurement of ocular accommodation basically comprises:
  a double-pass ophthalmoscopic system suitable for projecting a spot-light beam on a retina of an eye of a patient and capturing and processing an image resulting from the light which has been reflected in the retina of said spot-light beam;
  a periscopic system including a beam splitter aligned with respect to said spot-light beam and a mirror associated with an object in an open field;
  means for providing a controlled ocular accommodation stimulation through said periscopic system to generate at least one accommodation response;
  a Badal device, comprising two lenses and means for varying the distance therebetween to allow obtaining a series of images with different focus values on the retina; and
  means for recording and processing said images to select the one with the best optical quality from among them.

BRIEF DESCRIPTION OF THE DRAWINGS

To complement the description which is being made and for the purpose of aiding to better understand the features of the invention according to a preferred practical embodiment thereof, a set of figures is attached as an integral part of said description, in which the following has been depicted with an illustrative and non-limiting character:

FIG. 3 shows the general diagram of the method for determining the amplitude of accommodation based on the movement of the best double-pass image during the accommodative process. FIG. 3.a shows the double-pass images for different accommodative vergences, highlighting the best double-pass image in red. FIG. 3.b graphically depicts the accommodative response for each vergence of FIG. 3.a, and the method for determining the amplitude of accommodation.

DETAILED DESCRIPTION OF THE INVENTION

Figure 1:
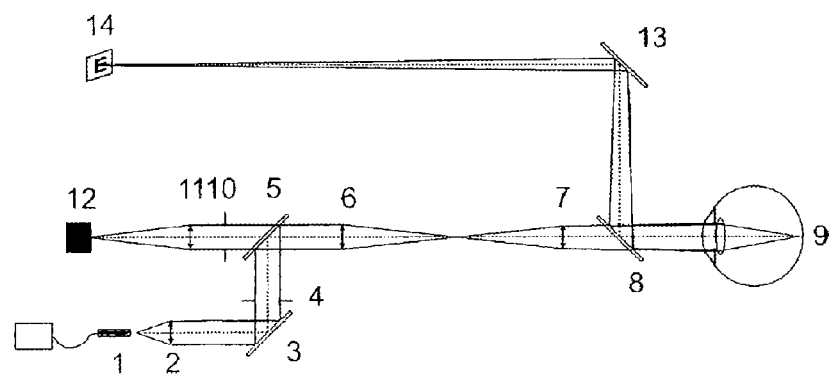
FIG. 1 shows the general diagram of the double-pass system incorporating an external fixation test.

FIG. 1 shows a diagram of the system of the present invention. The light coming from a laser diode coupled to an optical fiber 1 (or any other type of suitable light source, instead of using the optical fiber the laser can be spatially filtered) is collimated by means of a lens 2 and, after reflection in a mirror 3, it passes through a diaphragm 4 acting as an inlet pupil of the system. The light is reflected in a beam splitter 5 and traverses a Badal system formed by two lenses 6 and 7 which allows varying the vergence of the rays at the outlet thereof. The light traverses a beam splitter 8 by transmission and reaches the eye 9 of the patient, forming an image in the retina. After its reflection in the retina the light traverses in a reverse direction the beam splitter 8 and the lenses forming the Badal system 6 and 7. In the beam splitter 5 the light is transmitted and traverses a diaphragm 10 acting as an outlet pupil of the system. A lens 11 focuses the beam, forming an image in the CCD camera 12. During the image capturing process, the patient observes an externally located fixation test 14, the vergence of which is independent of that of the laser. The fixation test is seen through a mirror 13 and the beam splitter 8, where the optical paths of the fixation test and the laser converge.

Figure 2:
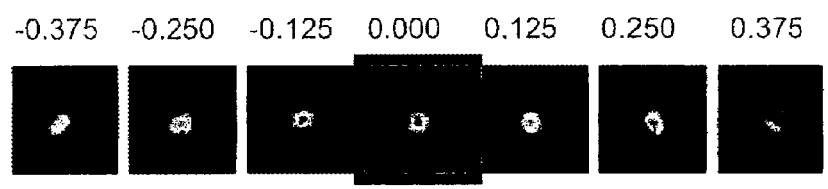
FIG. 2 shows the sequence of retinal images at a different vergence of the laser when the fixation test is maintained at constant vergence.

With the fixation test at a determined vergence, the measurement is usually started at 0 D, the vergence of the laser is changed by means of the Badal system and the double-pass images are recorded for each case. FIG. 2 shows a sequence of images at different vergences of the laser, whereas that of the fixation test remains constant, where the best image is highlighted in red and corresponds to that with a vergence of 0 D. This scan allows determining the refraction for far vision and is used as the zero of the system.

The process is repeated for different accommodative demands, either stimulating by means of moving the fixation test 14 of the figure closer or by means of adding negative lenses between the eye 9 of the observer and the beam splitter 8 of the FIG. 1. Depending on the method used, the reading of the vergence of the best double-pass image has a different meaning.

In the case of negative lenses, due to the fact that the laser is also affected by the dioptric power thereof, the difference of vergence between the best double-pass image of the accommodated and unaccommodated eye corresponds to the accommodative error, also known as accommodative lag. Once the accommodative lag is known, the accommodative response of the patient is calculated as the accommodative demand in diopters minus the accommodative error in diopters.

In the case of moving the fixation test closer, the difference of vergence between the best double-pass image in the accommodated and unaccommodated eye corresponds to the increase of the power of the eye due to accommodation, i.e., to the accommodative response.

In both methods, the accommodative demand is increased until detecting a drop of the response (because of the relaxation of the accommodative response due to the end of the accommodative range), and the amplitude of accommodation is calculated as the difference of the maximum and minimum accommodative response as shown in FIG. 3. In this example, the accommodative response increases up to a demand of 4 D; after that the response decreases, giving a result of an amplitude of accommodation of 3.5 D.

The invention claimed is:

1. A method for the objective measurement of ocular accommodation, comprising the following steps:
   projecting a spot-light beam on the retina of an eye of a patient;
   providing an ocular accommodation stimulation to generate an accommodative response;
   capturing and recording a series of images resulting from the light reflected in the retina of said spot-light beam in correspondence with the response to said stimulus, with a different focus position of the retina; and
   selecting, by processing, an image with the best optical quality from among said series of images, the focus value corresponding to said selected image providing the measurement of ocular accommodation.

2. The method according to claim 1, wherein said processing is carried out by means of an electronic processing system associated with an image capturing system.

3. The method according to claim 1, wherein said stimulation is carried out on the ciliary muscles of both eyes of said patient.

4. The method according to claim 1, wherein said capture is performed on a single eye of the patient and said stimulation is carried out on the ciliary muscles of said single eye.

5. The method according to claim 1, wherein said stimulation is carried out by means of a negative lens method.

6. The method according to claim 1, wherein said stimulation is carried out by means of a push-up method.

7. The method according to claim 1, wherein the mentioned steps, except for the step of stimulating, are carried out by means of using a double-pass ophthalmoscopic system.

8. The method according to claim 7, wherein said stimulation is carried out by means of a periscopic system including a beam splitter aligned with respect to said spot-light beam and a mirror associated with an object in an open field.

9. A system for the objective measurement of ocular accommodation comprising:
   a double-pass ophthalmoscopic system for projecting a spot-light beam on a retina of an eye of a patient and capturing and processing an image resulting from the light which has been reflected in the retina of said spot-light beam
   a periscopic system including a beam splitter aligned with respect to said spot-light beam and a mirror associated with an object in an open field;
   means providing an accommodation stimulation such that the ciliary muscle of said eye is stimulated through said periscopic system to generate at least one accommodation response;
   a Badal device, comprising two lenses and means for varying the distance therebetween to allow obtaining a series of images with different focus values on the retina; and
   means for recording and processing said images to select the one with the best optical quality from among them.

10. The system according to claim 9, wherein said means for stimulation comprise a system for moving said object closer to and away from said mirror of said periscopic system.

11. The system according to claim 9, wherein said means for stimulation comprise a set of exchangeable lenses of different diopters interposed between the eye of the patient and the object in an open field.

* * * * *

UNITED STATES PATENT AND TRADEMARK OFFICE
CERTIFICATE OF CORRECTION

PATENT NO.         : 8,366,270 B2
APPLICATION NO. : 12/990311
DATED              : February 5, 2013
INVENTOR(S)        : Pujol Ramo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 171 days.

Signed and Sealed this
First Day of September, 2015

Michelle K. Lee
*Director of the United States Patent and Trademark Office*